(12) United States Patent
Hubbell et al.

(10) Patent No.: US 6,350,527 B1
(45) Date of Patent: *Feb. 26, 2002

(54) GELS AND MULTILAYER SURFACE STRUCTURES FROM BORONIC ACID CONTAINING POLYMERS

(75) Inventors: Jeffrey A. Hubbell, Zumikon (CH); Donald L. Elbert, Lexington, KY (US); Natalie D. Winblade, Seattle, WA (US)

(73) Assignees: Eidgenossische Technische Hochschule Zurich; Universitat Zurich, both of Zurich (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/384,888

(22) Filed: Aug. 27, 1999

Related U.S. Application Data

(60) Provisional application No. 60/098,040, filed on Aug. 27, 1998.

(51) Int. Cl.$^7$ .................................................. B32B 9/04
(52) U.S. Cl. ........................ 428/473; 424/422; 424/423; 424/424; 424/425; 424/426
(58) Field of Search ................................ 424/422, 423, 424/424, 425, 426; 428/473

(56) References Cited

U.S. PATENT DOCUMENTS

| | | | |
|---|---|---|---|
| 4,716,203 A | 12/1987 | Casey et al. | 535/408 |
| 5,244,562 A | * 9/1993 | Russell | 204/418 |
| 5,410,016 A | 4/1995 | Hubbell et al. | 528/354 |
| 5,647,858 A | 7/1997 | Davidson | 609/264 |

FOREIGN PATENT DOCUMENTS

| | | |
|---|---|---|
| EP | 6339367 A | 4/1994 |
| WO | WO99/10022 A2 | 3/1999 |

OTHER PUBLICATIONS

Aoki, et al., "Effect of phenylboronic acid groups in copolymers on endothelial cell differentiation into capillary structures," *J. Biomater. Sci. Polym. Ed.* 9(1):1–14 (1997).
Aoki, et al., "Endothelial cell differentiation into capillary structures by copolymer surfaces with phenylborionic acid groups," *J. Biomater. Sci. Polym. Ed.* 7(7):539–50 (1995).
Choksakulnimitr, et al., "In vitro cytotoxicity of macromolecules in different cell culutre systems," *J. Contr. Rel.* 34:233–41 (1995).
Decher & Hong, "Buildup of ultrathin multilayer films by a self–assembly process: II. Consecutive adsorption of anionic and cationic bipolar amphiphiles and polyelectrolytes on charged surfaces," *Ber. Bunsenges. Phys. Chem.* 95:1430–1434 (1991).
Desai & Hubbell, "Surface modifications of polymeric biomaterials for reduced thrombogenicity," *Polym. Mater. Sci. Eng.* 62:731–735 (1990).
Diamond & Decherney, "Pathogenesis of adhesion formation/reformation: application to reproductive pelvic surgery," *Microsurgery.* 8(2):103–07 (1987).
Diamond, et al., "Synergistic effects of Interceed(TC7) and heparin in reducing adhesion formation in the rabbit uterine horn model," *Fertil. Steril.* 55(2):389–94 (1991).
Gibble & Ness, "Fibrin glue: the perfect operative sealant?" *Transfusion.* 30(8):741–7 (1990).
Han & Hubbell, "Lactide–based poly(ethylene glycol) polymer networks for scaffolds in tissue engineering," *Macromolecules* 29:5233–35 (1996).
Han & Hubbell, "Synthesis of polymer network scaffolds from $_L$–lactide and poly(ethylene glycol) and their interaction with cells," *Macromolecules* 30:6077–83 (1997).
Hubbell, "Hydrogel systems for barriers and local drug delivery in the control of wound healing," *J. Control. Rel.* 39:305–13 (1996).
Hubbell, et al., "Endothelial cell–selective materials for tissue engineering in the vascular graft via a new receptor," *Biotechnology (N Y).* 9(6):568–72 (1991).
Ikeya, et al., "Selective adhesion of rat lymphocyte subpopulation on the polymer surface with phenylboronic acid moieties: evaluation by field–flow fractionation/adhesion chromatography (FFF/AC) method," *Reactive & Functional Polymers* 37:251–261 (1998).
Interceed (TC7) Adhesion Barrier Study Group, "Prevention of postsurgical adhesions by Interceed (TC7), an absorbable adhesion barrier: a prospective, randomized multicenter clinical study," *Fertility and Sterility* 51:933–938 (1989).
Kikuchi, et al., "Glucose–sensing electrode coated with polymer complex gel containing phenylboronic acid," *Anal. Chem.* 68:823–828 (1996).
Leach & Henry, "Reduction of postoperative adhesions in the rat uterine horn model with poloxamer 407," *Am. J. Obstet. Gynecol.* 162(5):1317–19(1990).

(List continued on next page.)

*Primary Examiner*—Blaine Copenheaver
*Assistant Examiner*—Christopher Paulraj
(74) *Attorney, Agent, or Firm*—Holland & Knight LLP

(57) ABSTRACT

Boronic acid containing polymers are used to form bioinert gels and multilayer surface structures. These polymers form crosslinked hydrogels, which are highly swollen in water. The crosslinking can either be chemical or physical. Water soluble polymers containing boronic acid groups, such as phenylboronic acid (PBA), can be physically crosslinked by mixing the polymers in water with other polymers containing hydroxyls or carboxylic acids. Alternatively, surfaces can be treated by stepwise incubation with a solution of the boronic acid containing polymer, followed by incubation with a solution of a diol or carboxylic acid containing polymer. Many successive layers can be generated, increasing the thickness of the formed structure at each step. The bioinert gel or surface coating can be used for passivating the surfaces of medical implants (especially those based on transplanted tissue), or for passivating the surfaces of tissues in situ.

9 Claims, No Drawings

OTHER PUBLICATIONS

Linsky, et al., "Adhesion reduction in the rabbit uterine horn model using an absorbable barrier, TC–7," *J Reprod Med.* 32(1):17–20 (1987).

Lipatova, "Medical Polymer Adhesives," *Advances in Polymer Science* 79:65–93 (1986).

Liu & Scouten, "New ligands for boronate affinity chromatography," *Journal of Chromatography* A 687:61–69 (1994).

Miyazaki, et al., "Boronate–containing polymer as novel mitogen for lymphocytes," *Biochem Biophys Res Commun.* 195(2):829–36 (1993).

Sawhney & Hubbell, "Poly(ethylene oxide)–graft–poly(L–lysine) copolymers to enhance the biocompatibility of poly(L–lysine)–alginate microcapsule membranes," *Biomaterials.* 13(12):863–70 (1992).

Sawhney & Hubbell, "Rapidly degraded terpolymers of dl–lactide, glycolide, and epsilon–caprolactone with increased hydrophilicity by copolymerization with polyethers," *J. Biomed. Mater. Res.* 24(10):1397–411 (1990).

Sawhney, et al., "Interfacial photopolymerization of poly(ethylene glycol)–based hydrogels upon alginate–poly(I–lysine) microcapsyles for enhanced biocompatibility," *Biomaterials* 14:1008–1016 (1993).

Shiino, et al., "Amine effect on phenylboronic acid complex with glucose under physiological pH in aqueous solution," *J. Biomater. Sci. Polym. Ed.* 7(8):697–705 (1996).

Singhal, et al., "New ligands for boronate affinity chromatography: Synthesis and properties," *Journal of Chromatography* 543:17–38 (1991).

Steinleitner, et al., "Poloxamer 407 as an intraperitoneal barrier material for the prevention of postsurgical adhesion formation and reformation in rodent models for reproductive surgery." *Obstet Gynecol.* 77(1);48–52 (1991).

Thompson, et al., "Fibrin glue: a review of its preparation, efficacy, and adverse effects as a topical hemostat," *Drug Intell Clin Pharm.* 22(12):946–52 (1988).

Tsukagoshi, et al., "Preparation of phenylboronic acid–modified capillary and separation of nucleosides by capillary electrophoresis," *Analytical Sciences* 13:485–87 (1997).

Wulff, "Selective binding to polymers via covalent bonds. The construction of chiral cavities as soecufuc receptor sites," *Pure and Applied Chemistry* 54:2093–2102 (1982).

* cited by examiner

GELS AND MULTILAYER SURFACE STRUCTURES FROM BORONIC ACID CONTAINING POLYMERS

This application claims priority to U.S. Ser. No. 60/098,040 filed Aug. 27, 1998.

BACKGROUND OF THE INVENTION

This is generally in the field of polymeric materials for modulation of cell to cell interactions, especially for biomedical applications.

Hydrogels as Controlled-release Carriers

Biodegradable hydrogels can be carriers for biologically active materials such as hormones, enzymes, antibiotics, antineoplastic agents, and cell suspensions. Temporary preservation of functional properties of a carried species, as well as controlled release of the species into local tissues or systemic circulation, are possible. Proper choice of hydrogel macromers can produce membranes with a range of permeability, pore sizes and degradation rates suitable for a variety of applications in surgery, medical diagnosis and treatment.

Adhesives and Sealers

Polymeric hydrogels have also been used as tissue adhesives and sealants. Fibrin gels have been used extensively in Europe as sealants and adhesives in surgery (Thompson et al., 1988, *Drug Intell. and Clin. Pharm.,* 22:946; Gibble et al., 1990, (1990), *Transfusion,* 30(8):741). Synthetic polymers have been explored as adhesives (Lipatova, 1986, *Advances in Polymer Science* 79:65–93), but these materials have generally been associated with local inflammation, cytotoxicity, and poor biocompatability.

Prevention of Postoperative Adhesions.

Formation of post-surgical adhesions involving organs of the peritoneal cavity and the peritoneal wall is a frequent and undesirable result of abdominal surgery. Surgical trauma to the tissue caused by handling and drying results in release of a serosanguinous (proteinaceous) exudate which tends to collect in the pelvic cavity (Holtz, G., 1984). If the exudate is not absorbed or lysed within this period it becomes ingrown with fibroblasts, and subsequent collagen deposition leads to adhesion formation.

Numerous approaches to elimination of adhesion formation have been attempted, with limited success in most cases. Approaches have included lavage of the peritoneal cavity, administration of pharmacological agents, and the application of barriers to mechanically separate tissues. However, none of these approaches has been cost effective and effective in in vivo studies. Solutions of Poloxamer 407 have been used for the treatment of adhesions, with some success. Poloxamer is a copolymer of ethylene oxide and propylene oxide and is soluble in water; the solutions are liquids at room temperature. Steinleitner et al. (1991) *Obstetrics and Gynecology,* 77(1):48 and Leach et al. (1990) *Am. J. Obstet. Gynecol.,* 162(5):1317, examined Poloxamer solutions in peritoneal adhesion models and observed statistically significant reductions in adhesions; however, they were unable to eliminate adhesions, perhaps because of limited adhesion and retention on the injury site. Oxidized regenerated cellulose has also been used extensively to prevent adhesions and is an approved clinical product, trade-named Interceed TC7. This barrier material has been shown to be somewhat effective in rabbits (Linsky et al., 1987 *J. Reprod. Med.,* 32:17; Diamond et al., 1987 *Microsurgery,* 8:103) and in humans (Interceed (TC7) *Adhesion Barrier Study Group,* 1989). It was shown to be more effective if pretreated with heparin, but was still unable to completely eliminate adhesions (Diamond et al., 1991 "*Fertility and Sterility,* 55(2):389). U.S. Pat. No. 5,410,016 to Hubbell, et al., describes photopolymerizable biodegradable hydrogels as tissue contacting materials and controlled release carriers. These polymers included a water soluble region flanked by biodegradable linkers, terminated in photopolymerizable groups. Despite promising results in a rabbit model of adhesions, results of clinical trials to prevent adhesions following Cesarean sections were mixed, perhaps due to insufficient polymer thickness of the layers.

It is an object of the present invention to provide polymeric materials which form gels, coatings, and multi-layer structures that are bioinert and therefore useful for a variety of biomedical applications, including prevention of adhesions, as sealants, and for controlled delivery.

It is another object of the present invention to provide means for applying these polymeric materials to form coatings and medical devices.

SUMMARY OF THE INVENTION

Boronic acid containing polymers are used to form bioinert gels and multilayer surface structures. These polymers form crosslinked hydrogels, which are highly swollen in water. The crosslinking can either be chemical or physical. Water soluble polymers containing boronic acid groups, such as phenylboronic acid (PBA), can be physically crosslinked by mixing the polymers in water with other polymers containing hydroxyls or carboxylic acids. Alternatively, surfaces can be treated by stepwise incubation with a solution of the boronic acid containing polymer, followed by incubation with a solution of a diol or carboxylic acid containing polymer. Many successive layers can be generated, increasing the thickness of the formed structure at each step. Treatment of the surface is dependent upon the surface activity of the boronate containing polymer or the diol or carboxylic acid containing polymer, or the use of a priming layer, consisting of a molecule which has an affinity for the surface, as well as an affinity for the boronate containing polymer or the diol or carboxylic acid containing polymer. Priming may not be necessary in the case of binding to a cell or tissue surface, because the boronic acid domains bind to diols present in glycosylated proteins present in the cells.

The bioinert gel or surface coating can be used for passivating the surfaces of medical implants (especially those based on transplanted tissue), or for passivating the surfaces of tissues in situ, decreasing the incidence or severity of such pathologic conditions as the formation of post-surgical adhesions, and thrombosis following angioplasty.

DETAILED DESCRIPTION OF THE INVENTION

Boronic acid polymers are described for use in biomedical applications. In one embodiment, these are used in combination with diol or carboxylic acid containing polymers to form multilayer structures. The polymers and structures can be used for drug delivery, coatings or devices, or modified to alter cell attachment or interaction.

I. Boronic Acid Containing Compositions

Boronate Containing Polymers

Boronic Acid Polymers

Phenylboronic acid and its derivatives bind with high affinity to molecules containing vicinyl or closely opposed diols or carboxylic acids. This property has been previously exploited in biotechnology to produce glucose releasing devices (A. Kikuchi et al., *Anal. Chem.,* 68:823–828, 1996), chromatographic media with affinity for polysaccharides (K. Tsukagoshi et al., *Analytical Sciences,* 13:485–487, 1997), and as agents to interact with cell surfaces to promote cell attachment or receptor clustering (T. Aoki et al., *J. Biomat. Sci. Polym. Ed.,* 9:1–14, 1997; T. Ikeya et al, *Reactive & Functional Polymers,* 37:251–261, 1998).

Useful boronates include phenylboronic acid (PBA), 2-carboxyethaneboronic acid, 1,2-dicarboxyethaneboronic acid, β,β'-dicarboxyethaneboronate, β,γ-dicarboxypropaneboronate, 2-nitro- and 4-nitro-3-succinamidobenzene boronic acids, 3-nitro-4-(6-aminohexylamido)phenyl boronic acid, {4-[(hexamethylenetetramine)methyl]phenyl}boronic acid, 4-(N-methyl)carboxamidobenzene boronic acid, 2-{[(4-boronphenyl)methyl]-ethylammonio}ethyl and 2-{[(4-boronphenyl)methyl]diethylammonio}-ethyl groups, succinyl-3-aminophenylboronic acid, 6-aminocaproyl-3-aminophenylboronic acid, 3-(N-succinimidoxycarbonyl) aminophenylboronate, p-(ω-aminoethyl)phenylboronate, p-vinylbenzeneboronate, N-(3-dihydroxyborylphenyl)succinamic acid, N-(4-nitro-3-dihydroxyborylphenyl)succinamic acid, O-dimethylaminomethylbenzeneboronic acid, 4-carboxybenzeneboronic acid, 4-(N-octyl)carboxamidobenzeneboronic acid, 3-nitro-4-carboxybenzeneboronic acid, 2-nitro-4-carboxybenzeneboronic acid, 4-bromophenylboronate, p-vinylbenzene boronate, 4-(ω-aminoethyl)phenylboronate, catechol[2-(diethylamino)carbonyl, 4-bromomethyl] phenyl boronate, and 5-vinyl-2-dimethylaminomethylbenzeneboronic acid. These boronate containing groups differ in terms of pKa, spacer arms, or different coupling options associated with them.

In a preferred embodiment, the boronate group is provided by phenylboronic acid (PBA) which is known to form reversible conjugates with coplanar diols, such as closed ring carbohydrates and polyvinyl alcohol, as well as with acidic ligands such as dicarboxylic acids and α-hydroxy carboxylic acids. PBA has a strong affinity to many biological surfaces, since the surfaces of cells and extracellular matrix are rich in proteoglycans and other carbohydrate moieties, as well as many acidic moieties. PBA also has been shown to form reversible complexes with glycoconjugates on endothelial cell membranes (T. Aoki et al., *Journal of Biomaterials Science Polymer Edition* 7:539–550 (1995)) and lymphocyte membranes (H. Miyazaki et al., *Biochemical and Biophysical Research Communications* 195:829–836 (1993)).

The "working pH" of the PBA moieties in each copolymer can be adjusted by placing amine groups in proximity to the PBA groups or by placing electron withdrawing groups within the PBA moiety itself. A PBA moiety with a nitro group in the ring and a succinamic acid functionality has been synthesized by Singhal et al., *Journal of Chromatography* 543:17–38 (1991), and could be coupled to amine groups using carbonyldiimidazole or N-hydroxysuccinimide. A PBA moiety that has an internal coordinate bond, making the boron tetrahedral, and that has a bromomethyl group that could be reacted with the thiol of cysteine was synthesized by X.-C. Liu et al., *Journal of Chromatography A* 687:61–69 (1994). A polymer precursor with a very low pKa, 5-vinyl-2-dimethylaminomethylbenzeneboronic acid that could be used in creating random copolymers containing PBA was synthesized by G. Wulff, *Pure and Applied Chemistry* 54:2093–2102 (1982).

Any of a number of water soluble polymers incorporating any of the boronate groups listed above can be used as the boronate containing polymer. Such polymers are known in the art. Examples include poly(ethylene glycol), poly (ethylene oxide), poly(vinyl alcohol), poly (vinylpyrrolidone), poly(ethyloxazoline), poly(ethylene oxide)-co-poly(propyleneoxide) block copolymers such as polypropylene oxide-polyethylene oxide block copolymers, polysaccharides or carbohydrates such as hyaluronic acid, dextran, heparan sulfate, chondroitin sulfate, heparin, or alginate, and proteins such as gelatin, collagen, albumin, or ovalbumin. The term "at least substantially water soluble" is indicative that the solubility should be at least about 5 g,/100 ml of aqueous solution.

Synthesis of Boronate Containing Polymers

Polymers comprising phenylboronic acid moieties can be synthesized, for example, by reacting aminophenylboronic acid with acryloyl chloride (D. Shino et al., *J. Biomater. Sci Polym. Ed.,* 7:697–701, 1996), followed by free-radical polymerization with acrylamide to produce poly (acrylamide-co-acrylamidophenylboronic acid).

Diol or Carboxylic Acid Containing Polymer

The diol or carboxylic acid containing polymer can be, but is not limited to, dextran, mannan, polysialic acid, polyvinyl alcohol, hyaluronic acid, polyacrylic acid (or a derivative thereof such as methacrylic acid).

Synthesis of Copolymers

A copolymer of poly(acrylamide-co-acrylamidophenylboronic acid) and dextran can be synthesized by dissolving the poly(acrylamide-co-acrylamidophenylboronic acid) in buffered saline, and mixing the solution with dextran to form a gel. Phenylboronic acid does not bind to diols at a low pH, thus the pH of the solution could initially be at pH 5, then the pH could be raised to initiate gelation. The gelation could be induced to occur inside the body, for use in the prevention of post-surgical adhesions, by providing a barrier between tissues.

Polymer Modifications

The boronic acid containing polymers can have a number of other functionalities within the polymer chain, which can enhance such properties as water solubility, bioinertness, or charge. The diol or carboxylic acid containing polymers can be synthesized or selected so as to maximize bioinertness, or can be synthesized or selected to contain other functionalities that enhance such properties as water solubility, bioinertness, or charge. Additional polymeric components, domains, linking groups, and bioactive, prophylactic, or diagnostic materials can be added to either of the polymers to modify their properties.

Linking Groups or Polymers

Examples of additional polymeric components for attachment of linking groups or bioactive, prophylactic, or diagnostic materials include PEG, polyacrylic acid, poly-N-vinyl pyrrolidone, hyaluronic acid, and other polysaccharides. Other domains that can be incorporated into the boronic or diol or carboxylic acid containing polymers include bioadhesive molecules, domains which convert from a binding domain to a nonbinding domain in vivo, and domains which convert from a nonbinding domain to a binding domain in vivo, as described in U.S. Pat. No. 5,410,016 to Hubbell et al. Examples of linking groups include biodegradable linkages, such as anhydride, ester, amide, and carbonate linkages.

Materials Modifying Properties of the Polymeric Materials

The domains and/or linkages can be used to impart properties to the polymeric material. For example, domains may be incorporated into the polymer so that it selectively adheres to particular types of cells or molecules or is selectively degraded by enzymatic or nonenzymatic means. Degradation of the compositions can be controlled by the incorporation of sites that are degradable either chemically or enzymatically, providing a mechanism for the removal of the structure. The domains may consist of another polymer, for example, a biodegradable polymer such as a polyanhydride, polyhydroxy acid or polycarbonate, which makes the polymeric material biodegradable. Photopolymerizable substituents, including acrylates, diacrylates, oligoacrylates, dimethacrylates, or oligomethacrylates, and other biologically acceptable photopolymerizable groups, can also be coupled to the polymeric materials. These can be used to further polymerize the polymer once it is in contact with tissue or other surfaces, which can result in improved adherence to the surface.

Monomers or functional groups to be incorporated, as well as methods for incorporation, are known to those skilled in the art. The time required for a polymer to degrade can be tailored by selecting appropriate monomers. Differences in crystallinity also alter degradation rates. Due to the relatively hydrophobic nature of these polymers, actual mass loss only begins when the oligomeric fragments are small enough to be water soluble. Hence, initial polymer molecular weight influences the degradation rate. Degradable polymers containing water-soluble polymer elements have been described. For example, Sawhney et al., (1990) *J. Biomned. Mater. Res.* 24:1397–1411, copolymerized lactide, glycolide and ε-caprolactone with PEG to increase its hydrophilicity and degradation rate. U.S. Pat. No. 4,716,203 to Casey et al. (1987) also reports synthesis of PGA-PEG diblock copolymers, again with PEG ranging from 5–25%. Degradable materials of biological origin are well known, for example, crosslinked gelatin. Hyaluronic acid has been crosslinked and used as a degradable swelling polymer for biomedical applications (Della Valle et al. (1991) *Polym. Mater. Sci. Eng.,* 62:731–735]). U.S. Pat. No. 5,410,016 issued Apr. 25, 1995 describes biodegradable copolymers including water soluble polymers for use as photopolymerizable tissue coatings.and controlled release vehicles.

Materials to be Coupled to or Delivered Via the Polymers

Examples of bioactive materials which can be coupled to or incorporated within the polymeric materials include proteins and peptides, sugars and polysaccharides, organic compounds with drug activity, nucleic acids, and combinations thereof, such as glycoproteins and drug conjugates. A peptide such as RGD, or even a single amino acid, which is used to target a polyamino acid for cleavage by an enzyme, can be incorporated into the polymer structure, to direct attachment, or for subsequent polymer modification.

The bioactive, prophylactic, or diagnostic species can be attached to the copolymers, either covalently or ionically, or by mixing the species with the polymeric material, preferably before it is applied to tissue or used to form a device or multilayer structure.

A wide variety of biologically active materials can be encapsulated or incorporated, including proteins such as antibodies, receptor ligands and enzymes, peptides such as adhesion peptides, sugars, oligosaccharides, and polysaccharides, organic or inorganic drugs, nucleotides and nucleic acids, and cells, tissues or subcellular organelles or other subcellular components.

Exemplary ligands other than RGD include the pentapeptide Tyr-Ile-Gly-Ser-Arg (YIGSR), which supports endothelial, smooth muscle cell, and fibroblast adhesion, but not platelet adhesion; and the tetrapeptide Arg-Glu-Asp-Val (REDV), which has been shown to support endothelial cell adhesion but not that of smooth muscle cells, fibroblasts, or platelets, as described in Hubbell et al., *BioTechnology* 9:568–572 (1991). YIGSR, from laminin, binds to receptors on endothelial cells, but not on blood platelets. Thus, application of a copolymer having conjugated thereto the peptide YIGSR to a damaged vessel wall would be expected to block thrombosis on the vessel wall but not to block reendothelialization from the surrounding undamaged vessel wall.

Exemplary diagnostic agents include diagnostic enzymes and radiolabelled and fluorescent compounds.

II. Formation of Gels, Coatings, Devices and Multi-layer Structures

Boronic acid containing polymers are used to form bioinert gels and multilayer surface structures.

Formation of Gels and Coatings

The polymers form crosslinked hydrogels, which are highly swollen in water. The crosslinking can either be chemical or physical. Water soluble polymers containing boronic acid groups, such as phenylboronic acid (PBA), can be physically crosslinked by mixing the polymers in water with other polymers containing hydroxyls or carboxylic acids. As discussed below, multilayer structures are formed using alternating layers of boronic acid containing polymers and a diol or carboxylic acid containing polymer applied to each surface the boronic acid polymer is applied to, to provide sites for adhesion.

The boronate polymer can be applied in a fluid phase to the surface, such as tissues or cells, to be protected, whereupon the boronate groups adsorb the polymeric material to the surface. The fluid phase can be applied to isolated tissue or to tissue during surgery or by means of a catheter or other less invasive device. Priming is generally not necessary in the case where the solution is applied to cells or tissue surface, because the boronic acid domains bind to diols present in glycosylated proteins present in the cells.

Formation of Polymeric Multilayers

Multilayer techniques have been previously studied for surface modifications (G. Decher & J. Hong, *Ber. Bunsenges. Phys. Chem.* 95:1430–1434, 1991), and used to encapsulate living cells for transplantation (A. Sawhney et al., *Biomaterials,* 13:863–870, 1992). Previous work has utilized polycations and polyanions, which also form gels when mixed in certain proportions under certain conditions.

The use of the boronic acid polymers described herein to form multilayers of polymers avoids some of the toxicity problems associated with the polycation and polyanion materials. Surfaces can be treated by stepwise incubation with a solution of the boronic acid containing polymer, followed by incubation with a solution of a diol or carboxylic acid containing polymer to generate many successive layers, increasing the thickness of the formed structure at each step. Treatment of the surface is dependent upon the surface activity of the boronate containing polymer or the diol or carboxylic acid containing polymer, or the use of a priming layer, consisting of a molecule which has an affinity for the surface, as well as an affinity for the boronate containing polymer or the diol or carboxylic acid containing polymer. These molecules do not interact via salt bridge formation, avoiding the extreme toxicity of polycationic molecules when in solution (S. Choksakulnimitr et al., *J. Contr. Rel.,* 34:233–241, 1995) which is an issue during application of the polycationic/polyanionic structure, and during degradation of the structure. The bioinertness of such materials may also be higher when at least one of the components is nonionic.

As noted above, the boronate polymer can be applied in a fluid phase to the surface, such as tissues or cells, to be protected, where the cells or tissue is in isolated form or during surgery or by means of a catheter or other less invasive device. The diol or carboxylic acid polymer is then added in a fluid phase and crosslinks the already applied boronate polymer.

This process is repeated until the desired thickness is obtained. This process is referred to herein as "multilayer techniques". If only a monolayer of each boronate containing polymer adsorbs with each incubation, then the coating can be built on a surface a few microns at a time. There are preferably greater than five alternating layers, more preferably more than ten alternating layers, and most preferably, greater than fifteen alternating layers of the polymers.

In another embodiment, the surface is not thoroughly rinsed between the application of the polymers. This leads to the formation of thicker structures. An apparatus equipped with a spray nozzle can be used, for example, to spray a layer at a time of a boronate containing polymer followed by a layer of a diol or carboxylic acid containing polymer. Alternatively, both polymers can be sprayed simultaneously to create relatively thicker layers.

Thickness of the coating can be varied by selection of the reaction components and/or the reaction conditions. For example, the layer thickness can be controlled by adjusting the number of layers and also the degree of rinsing between layers. Control of drop size and density during spraying of polymer yields coatings of the desired thickness without necessarily requiring rinsing between layers. Additionally, the excess (unbound) material can be removed via other means, for example, by an air jet. The polymer systems can be used to generate thick, non-adhesive films by increasing the number of cycles, for example, to 50 or higher.

Implant or Device Coatings

The boronic acid polymer is preferably applied to a device having on its surface sites crosslinking with the boronic acid polymer. This can be achieved either by selection of a substrate with suitable functional groups, or by application to the surface of a solution of a polymeric material containing diol and/or carboxyl groups. For example, a buffered solution of poly(acrylamide-co-acrylamidephenylboronic acid) can be incubated with a porcine valve implant, followed by washing with buffered saline. The implant can then be incubated with a buffered solution of hyaluronic acid, dextran, or polysialic acid, followed by washing. This process could be repeated five or more times to produce a bioinert surface coating on the implant, of varying thickness depending upon the number of repetitions.

III. Methods of Using the Compositions

Multilayers of the polymers can be formed on macroscopic tissue surfaces, including mammalian tissue surfaces, and thereby provide various benefits to the coated surfaces. These include the prevention of adherence of tissue to tissue, or of cells to tissue, or provision of selective adherence, as described below. The layers can be used to encapsulate, plug, seal, or support a macroscopic surface. The application of a multilayer coating can be used to minimize or prevent tissue adhesion, minimize or prevent postoperative adhesions, prevent thrombosis, prevent implantation of cancerous cells, coat tissue to encourage healing or prevent infection, or enhance the local delivery of bioactive agents. Preferably, at least four layers, and, more preferably, at least six layers, are used to form the coatings.

The compositions, while serving as bioinert scaffolds, can also serve to provide biospecific signaling.

The same type of technique can be used to coat the inside of an artery following balloon angioplasty, to reduce thrombosis; to coat the surface of red blood cells to enhance the efficacy of blood transfusion; to coat a tissue engineered implant, and to coat a tissue which has been damaged during surgery.

Publications cited herein and the material for which they are cited are specifically incorporated by reference. Modifications and variations of the present invention will be obvious to those skilled in the art from the foregoing detailed description and are intended to be encompassed by the following claims.

We claim:

1. A coating which minimizes or prevents tissue adhesion on the surface of cells, tissue, or a device for implantation into a patient comprising a polymer containing more than one boronic acid group crosslinked with a polymer containing more than one hydroxyl or carboxylic acid functional group or device substrate containing more than one hydroxyl or carboxylic acid functional group.

2. The coating of claim 1, comprising alternating layers of the polymer containing more than one boronic acid group and a polymer containing more than one hydroxyl or carboxylic acid functional group.

3. The coating of claim 2 wherein the polymer containing more than one hydroxyl or carboxylic acid functional group is applied onto the surface of the cells or tissue.

4. The coating of claim 2 comprising at least five layers of polymer.

5. The coating of claim 1 wherein the polymer containing more than one hydroxyl or carboxylic acid functional group is a water soluble polymer.

6. The coating of claim 1 wherein the substrate is the surface of a medical device.

7. The coating of claim 1 further comprising an agent selected from the group consisting of therapeutic, prophylactic or diagnostic agents, coupled to or incorporated in, the polymer.

8. The coating of claim 1 wherein the polymer containing more than one boronic acid group comprises functional groups or domains modifying the polymer properties.

9. The coating of claim 8 wherein the polymer comprises biodegradable groups or domains.

* * * * *